United States Patent [19]
Curtis et al.

[11] Patent Number: 5,849,765
[45] Date of Patent: Dec. 15, 1998

[54] TETRAHYDROPYRIDINE DERIVATIVES AS DOPAMINE RECEPTOR SUBTYPE LIGANDS

[75] Inventors: Neil Roy Curtis, Puckeridge; Janusz Jozef Kulagowski, Sawbridgeworth; Paul David Leeson, Melbourne; Kevin William Moore, Buntingford; Andrew Pate Owens, Rushden; Martin Richard Teall, Stansted, all of England

[73] Assignee: Merck Sharp & Dohme, Ltd., Hoddesdon, England

[21] Appl. No.: 813,748

[22] Filed: Mar. 7, 1997

[30] Foreign Application Priority Data

Mar. 11, 1996 [GB] United Kingdom .................... 9605065

[51] Int. Cl.$^6$ ............................................. A61K 31/425
[52] U.S. Cl. ...................... 514/338; 514/337; 514/339; 546/270.1; 546/271.7; 546/273.4; 546/277.4; 546/280.4; 546/284.1
[58] Field of Search .................... 546/270.1; 514/338

[56] References Cited

U.S. PATENT DOCUMENTS

| | | | |
|---|---|---|---|
| 3,478,046 | 11/1969 | Sarett | 546/270.1 |
| 4,169,200 | 9/1979 | Hauck et al. | 546/271.7 |
| 5,412,099 | 5/1995 | Goldman | 546/270.1 |
| 5,635,519 | 6/1997 | Okamoto et al. | 546/270.1 |
| 5,700,809 | 12/1997 | Leeson et al. | 514/300 |
| 5,712,285 | 1/1998 | Curtis | 514/300 |
| 5,773,434 | 6/1998 | Larson et al. | 574/338 |

FOREIGN PATENT DOCUMENTS

| | | |
|---|---|---|
| 4864077 | 9/1973 | Japan . |
| WO 94/21615 | 9/1994 | WIPO . |
| WO9420459 | 9/1994 | WIPO . |

OTHER PUBLICATIONS

Baldaress Arini et al. New Eng. Jour Med vol. 324 pp. 746–754, 1991.
Kadis, Chem. Abstracts vol. 82 Entry 66062, 1975.
Van Tol et al, Nature vol. 350 pp. 610–614 (1991).

*Primary Examiner*—Donald G. Daus
*Attorney, Agent, or Firm*—Philippe L. Durette; Melvin Winokur

[57] ABSTRACT

A class of 1,2,3,6-tetrahydropyridine derivatives, substituted in the 4-position by a fused bicyclic heteroaromatic moiety and in the 1-position by an optionally substituted benzyl moiety, are ligands for dopamine receptor subtypes within the body, in particular the $D_4$ subtype, and are therefore useful in the treatment and/or prevention of disorders of the dopamine system, in particular schizophrenia or depression.

8 Claims, No Drawings

TETRAHYDROPYRIDINE DERIVATIVES AS DOPAMINE RECEPTOR SUBTYPE LIGANDS

This invention relates to the therapeutic use of a particular class of heterocyclic compounds. More particularly, the invention is concerned with the therapeutic use of substituted tetrahydropyridine derivatives which have been found to be ligands for dopamine receptor subtypes within the body, in particular the dopamine $D_4$ receptor subtype. These compounds are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., *Biol. Psychiatry*, 1993, 34, 459).

Upper gastrointestinal tract motility is believed to be under the control of the dopamine system. The compounds of use in the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds of use in the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of use in the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds of use in the present invention may therefore be of assistance in the prevention and/or treatment of such conditions as hypertension and congestive heart failure.

By virtue of their activity as ligands for dopamine receptor subtypes within the body, the compounds of use in the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature (London)*, 1991, 350, 610) and $D_5$ (Sunahara et al., *Nature (London)*, 1991, 350, 614) receptor subtypes have been described.

JP-A-4864077 describes a class of substituted tetrahydropyridine derivatives which are stated to have utility as analgesics and anti-inflammatories.

Certain N-benzyl-1,2,3,6-tetrahydropyridine derivatives are described as intermediates in WO-A-94/20459. However, no therapeutic utility is ascribed therein to the N-benzyl-1,2,3,6-tetrahydropyridine intermediates described in WO-A-94/20459.

The compounds of use in the present invention, being ligands for dopamine receptor subtypes within the body, in particular the $D_4$ receptor subtype, are accordingly of use in the treatment and/or prevention of disorders of the dopamine system, including schizophrenia and depression.

The present invention provides a method for the prevention and/or treatment of clinical conditions for which a dopamine receptor subtype ligand, in particular a selective ligand for the dopamine $D_4$ receptor subtype, is indicated, which method comprises administering to a patient in need of such treatment an effective amount of a compound of formula I, or a pharmaceutically acceptable salt thereof:

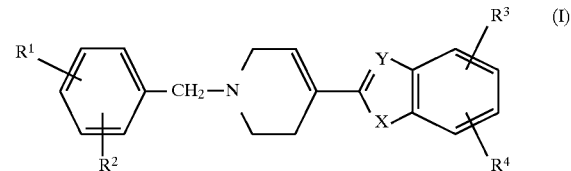

wherein
X represents oxygen, sulphur or NH;
Y represents CH or nitrogen; and
$R^1$, $R^2$, $R^3$ and $R^4$ independently represent hydrogen, halogen, cyano, nitro, trifluoromethyl, $C_{1-6}$ alkyl or $C_{1-6}$ alkoxy.

In another aspect, the present invention provides the use of a compound of formula I as defined above or a pharmaceutically acceptable salt thereof for the manufacture of a medicament for the prevention and/or treatment of clinical conditions for which a dopamine receptor subtype ligand, in particular a selective ligand for the dopamine $D_4$ receptor subtype, is indicated.

As used herein, the expression "$C_{1-6}$ alkyl" relates to methyl and ethyl groups, and straight-chained or branched propyl, butyl, pentyl and hexyl groups. Particular alkyl groups include methyl, ethyl, n-propyl, isopropyl and tert-butyl. Derived expressions such as "$C_{1-6}$ alkoxy" are to be construed accordingly.

The term "halogen" as used herein includes fluorine, chlorine, bromine and iodine, especially fluorine or chlorine.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof in any proportion is encompassed within the scope of the present invention.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

When Y in the compounds of formula I above represents CH, X suitably represents oxygen or sulphur. When Y represents nitrogen, X suitably represents oxygen, sulphur or NH.

Examples of suitable values for the substituent $R^1$ include hydrogen, fluoro, chloro, bromo, cyano, nitro, methyl and methoxy.

Suitably, $R^2$ represents hydrogen or chloro.

Suitable values for the group $R^3$ include hydrogen, chloro, trifluoromethyl, methyl and methoxy.

Suitably, $R^4$ represents hydrogen or methyl, typically hydrogen.

In a further aspect, the present invention provides a pharmaceutical composition comprising one or more of the following compounds:

1-benzyl-4-(benzothiophen-2-yl)-1,2,3,6-tetrahydropyridine;
1-benzyl-4-(benzofuran-2-yl)-1,2,3,6-tetrahydropyridine;
and pharmaceutically acceptable salts thereof; in association with a pharmaceutically acceptable carrier.

The present invention also provides a compound selected from the following:

1-benzyl-4-(benzothiophen-2-yl)-1,2,3,6-tetrahydropyridine;
1-benzyl-4-(benzofuran-2-yl)-1,2,3,6-tetrahydropyridine;
and pharmaceutically acceptable salts thereof; for use in therapy.

Certain specific compounds falling within the scope of formula I above are novel. In a still further aspect, therefore, the invention provides a compound selected from the following:

4-(benzothiophen-2-yl)-1-(4-chlorobenzyl)-1,2,3,6-tetrahydropyridine;
4-(benzothiophen-2-yl)-1-(3-chlorobenzyl)-1,2,3,6-tetrahydropyridine;
4-(benzothiophen-2-yl)-1-(2-chlorobenzyl)-1,2,3,6-tetrahydropyridine;
4-(benzothiophen-2-yl)-1-(3,4-dichlorobenzyl)-1,2,3,6-tetrahydropyridine;
4-(benzothiophen-2-yl)-1-(4-fluorobenzyl)-1,2,3,6-tetrahydropyridine;
4-(benzothiophen-2-yl)-1-(4-methoxybenzyl)-1,2,3,6-tetrahydropyridine;
4-(benzothiazol-2-yl)-1-benzyl-1,2,3,6-tetrahydropyridine;
4-(benzothiazol-2-yl)-1-(4-chlorobenzyl)-1,2,3,6-tetrahydropyridine;
4-(benzothiazol-2-yl)-1-(3-chlorobenzyl)-1,2,3,6-tetrahydropyridine;
4-(enzothiazol-2-yl)-(2-chlorobenzyl)-1,2,3,6-tetrahydropyridine;
4-(benzothiazol-2-yl)-1-(4-cyanobenzyl)-1,2,3,6-tetrahydropyridine;
1-benzyl-4-(5-chlorobenzothiazol-2-yl) -1,2,3,6-tetrahydropyridine;
4-(5-chlorobenzothiazol-2-yl)-1-(4-chlorobenzyl)-1,2,3,6-tetrahydropyridine;
4-(5-chlorobenzothiazol-2-yl)-1-(3-chlorobenzyl)-1,2,3,6-tetrahydropyridine;
4-(5-chlorobenzothiazol-2-yl)-1-(2-chlorobenzyl)-1,2,3,6-tetrahydropyridine;
1-benzyl-4-(5-trifluoromethylbenzothiazol-2-yl) -1,2,3,6-tetrahydropyridine;
4-(benzoxazol-2-yl)-1-benzyl-1,2,3,6-tetrahydropyridine;
4-(5-chlorobenzoxazol-2-yl)-1-benzyl-1,2,3,6-tetrahydropyridine;
4-(5-chlorobenzoxazol-2-yl)-1-(3-clorobenzyl)-1,2,3,6-tetrahydropyridine;
4-(5-chlorobenzoxazol-2-yl)-1-(4-chlorobenzyl)-1,2,3,6-tetrahydropyridine;
4-(5-chlorobenzoxazol-2-yl) 1-(4-fluorobenzyl)-1,2,3,6-tetrahydropyridine;
4-(5-chlorobenzoxazol-2-yl)-1-(4-methylbenzyl)-1,2,3,6-tetrahydropyridine;
4-(5-chlorobenzoxazol-2-yl)-1-(4-methoxybenzyl)-1,2,3,6-tetrahydropyridine;
1-benzyl-4-(6-methylbenzoxazol-2-yl)-1,2,3,6-tetrahydropyridine;
1-benzyl-4-(4-methylbenzoxazol-2-yl)-1,2,3,6-tetrahydropyridine;
1-benzyl-4-(5-methylbenzoxazol-2-yl)-1,2,3,6-tetrahydropyridine;
1-benzyl-4-(benzimidazol-2-yl)-1,2,3,6-tetrahydropyridine;
4-(benzimidazol-2-yl)-1-(4-cyanobenzyl)-1,2,3,6-tetrahydropyridine;
4-(benzimidazol-2-yl)-1-(4-bromobenzyl)-1,2,3,6-tetrahydropyridine;
4-(benzimidazol-2-yl)-1-(4-methoxybenzyl)-1,2,3,6-tetrahydropyridine;
4-(benzimidazol-2-yl)-1-(3,4-dichlorobenzyl)-1,2,3,6-tetrahydropyridine;
4-(benzimidazol-2-yl)-1-(4-chlorobenzyl)-1,2,3,6-tetrahydropyridine;
1-(4-chlorobenzyl)-4-(4-methylbenzimidazol-2-yl)-1,2,3,6-tetrahydropyridine;
1-(4-chlorobenzyl)-4-(4,5-dimethylbenzimidazol-2-yl)-1,2,3,6-tetrahydropyridine;
1-benzyl-4-(5-chlorobenzimidazol-2-yl)-1,2,3,6-tetrahydropyridine;
4-(5-chlorobenzimidazol-2-yl)-1-(4-chlorobenzyl)-1,2,3,6-tetrahydropyridine;
4-(5-chlorobenzimidazol-2-yl)-1-(3-chlorobenzyl)-1,2,3,6-tetrahydropyridine;
4-(5-chlorobenzimidazol-2-yl)-1-(2-chlorobenzyl) -1,2,3,6-tetrahydropyridine;
1-(3-chlorobenzyl)-4-(5-trifluoromethylbenzimidazol-2-yl)-1,2,3,6-tetrahydropyridine;
1-(4-chlorobenzyl)-4-(5-methoxybenzimidazol-2-yl)-1,2,3,6-tetrahydropyridine;
and pharmaceutically acceptable salts thereof.

The invention also provides pharmaceutical compositions comprising one or more of the novel compounds of this invention in association with a pharmaceutically acceptable carrier.

The compositions in accordance with the present invention are suitably in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia or depression, a suitable dosage level is about 0.001 to 250 mg/kg per day, preferably about 0.005 to 100 mg/kg per day, and especially about 0.01 to 5 mg/kg per day. The compounds may be administered on a regimen of 1 to 4 times per day.

In order to alleviate the symptoms of schizophrenia without causing sedation or extrapyramidal side-effects, it is believed that the dosage level of the active ingredient should be selected such that the dose administered is effective in substantially completely blocking the dopamine $D_4$ receptor subtype in human brain whilst displaying no or negligible $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the compounds of use in this invention may be co-administered with another medicament, for example a known anti-schizophrenic agent which produces its effects via dopamine $D_2$ and/or $5\text{-}HT_2$ receptor blockade. Such co-administration may be desirable where a patient is already on an established treatment regime, for example one involving conventional anti-schizophrenic medicaments such as haloperidol or chlorpromazine.

The compounds of formula I above, including the novel compounds according to the invention, may be prepared by a process which comprises reacting a compound of formula II with a compound of formula III:

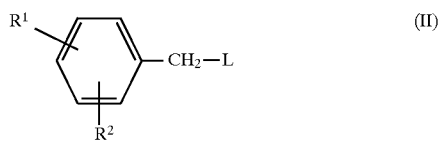

(II)

-continued

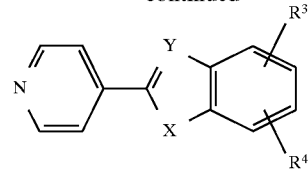

(III)

wherein X, Y, $R^1$, $R^2$, $R^3$ and $R^4$ are as defined above, and L represents a suitable leaving group; followed by treatment of the resulting pyridinium salt with a reducing agent.

The leaving group L is suitably a halogen atom, e.g. chlorine or bromine; or a $C_{1-6}$ alkylsulphonyloxy group, e.g. methanesulphonyloxy (mesyloxy).

Where L represents a halogen atom, the reaction between compounds II and III is conveniently effected in a suitable solvent, e.g. N,N-dimethylformamide, typically at an elevated temperature.

Reduction of the pyridinium salt is conveniently brought about by treatment with a reducing agent such as sodium borohydride, typically in a lower alkanol such as ethanol.

In an alternative procedure, the compounds of formula I above, including the novel compounds according to the invention, may be prepared by a process which comprises reacting a compound of formula IV with the anion of a compound of formula V:

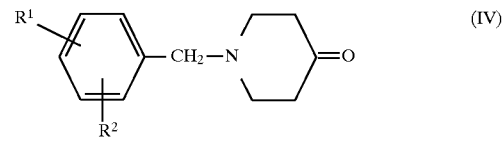

(IV)

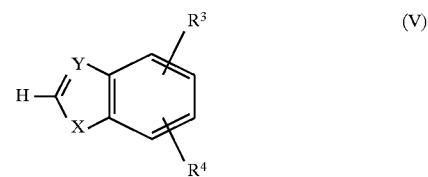

(V)

wherein X, Y, $R^1$, $R^2$, $R^3$ and $R^4$ are as defined above; followed by treatment of the resulting 4-hydroxypiperidine derivative with a dehydrating agent.

The anion of compound V is suitably generated by treating the appropriate compound of formula V with an alkyllithium reagent, e.g. n-butyllithium, in an inert solvent such as tetrahydrofuran.

The reaction between compound IV and the anion of compound V is conveniently effected by stirring the reactants at room temperature in a suitable solvent, e.g. tetrahydrofuran.

The resulting 4-hydroxypiperidine intermediate may be isolated and purified before being dehydrated, or the dehydration step may be performed in situ on the reaction mixture. Dehydration of the 4-hydroxypiperidine derivative is conveniently brought about by treatment with an acidic reagent such as trifluoroacetic acid or p-toluenesulphonic acid.

In a further procedure, the compounds of formula I above, including the novel compounds according to the invention, may be prepared by a process which comprises reacting a compound of formula II as defined above with a compound of formula VI:

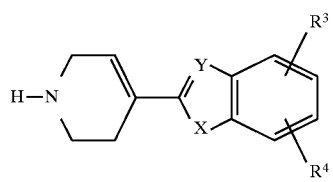

(VI)

wherein X, Y, $R^3$ and $R^4$ are as defined above.

The reaction is conveniently carried out under basic conditions in a suitable solvent, e.g. potassium carbonate in N,N-dimethylformamide.

The intermediates of formula VI above may be prepared by deprotection of a compound of formula VII:

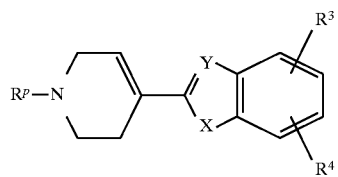

(VII)

wherein X, Y, $R^3$ and $R^4$ are as defined above, and $R^P$ represents an amino-protecting group.

The amino-protecting group $R^P$ is suitably benzyl, which can conveniently be removed as necessary by treating compound VII with 1-chloroethyl chloroformate in a solvent such as dichloromethane, followed by heating under reflux in methanol.

Where they are not commercially available, the starting materials of formula II, III, IV, V and VII may be prepared by methods analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. Indeed, as will be appreciated, the compounds of formula VII wherein $R_p$ is benzyl are compounds of use in the invention in their own right.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds of use in the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [3H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and were found to possess a $K_i$ value for displacement of [$^3$H]-spiperone from the human dopamine $D_4$ receptor subtype of below 1.5 μM in each case.

EXAMPLE 1

4-(Benzothiophen-2-yl)-1-(4-chlorobenzyl)-1,2,3,6-tetrahydropyridine

Step 1: 4-(Benzothiophen-2-yl)-1-benzyl-4-hydroxypiperidine

Benzothiophene (10 g, 0.07 mol) was dissolved in tetrahydrofuran (150 ml) and cooled to −10° C. (ice/methanol). Butyl lithium (33 ml of 2.5M in hexane, 0.077 mol) was added dropwise and the reaction mixture warmed to room temperature over one hour. Following addition of N-benzyl piperidone (9.16 ml, 0.07 mol) at −40°, the reaction was stirred overnight at room temperature. The reaction mixture was concentrated in vacuo and the crude product purified by flash chromatography eluting with 20% and 30% ethyl acetate in petroleum ether to give an orange/red solid. Recrystallisation from ether afforded the title compound as a pale yellow solid (16.87g, 75%); $δ_H$ ($CDCl_3$), 1.96 (2H, m, $NCH_2CH_2$), 1.99 (1H, s, OH), 2.25 (2H, t of d, J 13.5Hz, J 4.4Hz, $NCH_2CH_2$), 2.51 (2H, t of d, J 11.6Hz, J 2.46Hz, $NCH_2CH_2$), 2.76 (2H, m, $NCH_2CH_2$), 3.57 (2H, s, $NCH_2$, Ar), 7.30 (8H, m, ArH), 7.70 (1H, d, J 7Hz, ArH), 7.79 (1H, d, J 7.6Hz, ArH). m/z ($ES^+$) 324 (M+1)$^+$.

Step 2: 4-(Benzothiophen-2-yl)-1-benzyl-1,2,3,6-tetrahydropyridine 4-(Benzothiophen-2-yl)-1-benzyl-4-hydroxypiperidine (4.5 g, 0.01 mol) was dissolved in trifluoroacetic acid (50 ml) and stirred at room temperature overnight. The reaction mixture was concentrated in vacuo and the residue partitioned between aqueous saturated potassium carbonate solution and dichloromethane (3×100 ml). The combined organic layers were washed with brine (200 ml), dried ($MgSO_4$) and concentrated. The crude product was purified by flash chromatography eluting with 10% ethyl acetate in petroleum ether. Concentration of the appropriate fractions gave the title compound as a pale yellow solid (3.5 g, 82%);

$\delta_H$ (CDCl$_3$), 2.63 (2H, m, NCH$_2$CH$_2$), 2.73 (2H, m, NCH$_2$CH$_2$), 3.19 (2H, m, NCH$_2$CH$_2$), 3.64 (2H, s, NCH$_2$Ar), 6.19 (1H, m, NCH$_2$CH), 7.11 (1H, s, ArH), 7.31 (7H, m, ArH), 7.65 (1H, d of d, J 6.4Hz, J 1.9Hz, ArH), 7.72 (1H, d of d, J 6.9Hz, J 1.8Hz, ArH). m/z (ES$^+$) 306 (M+1)$^+$.

Step 3: 4-(Benzothiophen-2-yl)-1,2,3,6-tetrahydropyridine hydrochloride

To a solution of 4-(benzothiophen-2-yl)-1-benzyl-1,2,3,6-tetrahydropyridine (3.5 g, 0.01 mol) in anhydrous dichloromethane (50 ml) cooled in ice was added chloroethyl chloroformate (1.61 ml, 0.013 mol). The reaction was stirred at room temperature for 1½ hours and concentrated in vacuo. The residue was suspended in methanol (25 ml) and stirred under reflux for 1 hour. The reaction mixture was cooled, and the resultant solid isolated by filtration, to afford the title compound as a pale yellow solid (2.1 g, 84%). $\delta_H$ (DMSO-d$_6$), 2.80 (2H, m, HNCH$_2$CH$_2$), 3.34 (2H, m, HNCH$_2$CH$_2$), 3.77 (2H, m, HNCH$_2$CH$_2$), 6.21 (1H, m, HNCH$_2$CH), 7.35 (2H, m, ArH), 7.49 (1H, s, ArH), 7.81 (1H, m, ArH), 7.92 (1H, m, ArH).

Step 4: 4-(Benzothiophen-2-yl)-1-(4-chlorobenzyl)-1,2,3,6-tetrahydropyridine 4-(Benzothiophen-2-yl)-1,2,3,6-tetrahydropyridine hydrochloride (250 mg, 0.99 mmol) was dissolved in DMF (5 ml), potassium carbonate (412 mg, 2.9 mmol) added, and the reaction mixture stirred at room temperature for 10 minutes. 4-Chlorobenzyl bromide (306 mg, 1.5 mmol) was added and the resulting reaction mixture stirred at room temperature overnight. After dilution with water (50 ml), the product was extracted into ethyl acetate (3×40 ml). The combined organic layers were washed with brine (100 ml), dried (MgSO$_4$) and concentrated. The crude product was triturated with methanol to yield a pale brown solid. Recrystallisation from hot dichloromethane and methanol gave the title compound as a pale yellow solid (60 mg, 18%); (Found: C, 70.33; H, 5.20; N, 4.16. C$_{20}$H$_{18}$ClNS requires C, 70.68; H, 5.34; N, 4.12%); $\delta_H$ (CDCl$_3$), 2.64 (2H, m, NCH$_2$CH$_2$), 2.72 (2H, m, NCH$_2$CH$_2$), 3.18 (2H, m, NCH$_2$CH$_2$), 3.61 (2H, s, NCH$_2$Ar), 6.18 (1H, m, NCH$_2$CH), 7.12 (1H, s, ArH), 7.28 (6H, m, ArH), 7.66 (1H, d of d, J 6Hz, J 2Hz, ArH), 7.74 (1H, d of d, J 6.7Hz, J 2Hz, ArH). m/z (ES$^+$) 340 (M+1)$^+$.

EXAMPLE 2

4-(Benzothiophen-2-yl)-1-(3-chlorobenzyl)-1,2,3,6-tetrahydropyridine 4-(Benzothiophen-2-yl)-1,2,3,6-tetrahydropyridine hydrochloride (250 mg, 0.99 mmol) was reacted with 3-chlorobenzyl bromide (0.2 ml, 1.5 mmol) as exemplified in Example 1. The crude product was triturated with methanol to give the title compound as a pale yellow solid (50 mg, 15%); (Found: C, 69.05; H, 5.03; N, 4.07. C$_{20}$H$_{18}$ClNS. 0.5H$_2$O requires C, 68.85; H, 5.49; N, 4.01%). $\delta_H$ (CDCl$_3$), 2.65 (2H, m, NCH$_2$CH$_2$), 2.73 (2H, m, NCH$_2$CH$_2$), 3.18 (2H, m, NCH$_2$CH$_2$), 3.62 (2H, s, NCH$_2$Ar), 6.19 (1H, m, NCH$_2$CH), 7.12 (1H, s, ArH), 7.28 (5H, m, ArH), 7.39 (1H, s, ArH), 7.67 (1H, d of d, J 6.2Hz, J 1.9Hz, ArH), 7.73 (1H, d of d, J 8.4Hz, J 1.8Hz, ArH). m/z (ES$^+$) 340 (M+1)$^+$.

EXAMPLE 3

4-(Benzothiophen-2-yl)-1-(2-chlorobenzyl)-1,2,3,6-tetrahydropyridine 4-(Benzothiophen-2-yl)-1,2,3,6-tetrahydropyridine hydrochloride (250 mg, 0.99 mmol) was reacted with 2-chlorobenzyl bromide (0.24 ml, 1.5 mmol) as exemplified in Example 1. The crude product was triturated with methanol to give the title compound as a pale yellow brown solid (40 mg, 12%) m.p. 105°–106° C.; (Found: C, 69.29; H, 5.17; N, 4.23. C$_{20}$H$_{18}$ClNS. 0.5H$_2$O requires C, 68.85; H, 5.49; N, 4.01%). $\delta_H$ (CDCl$_3$), 2.66 (2H, m, NCH$_2$CH$_2$), 2.80 (2H, m, NCH$_2$CH$_2$), 3.27 (2H, m, NCH$_2$CH$_2$), 3.77 (2H, s, NCH$_2$Ar), 6.20 (1H, m, NCH$_2$CH), 7.13 (1H, s, ArH), 7.25 (4H, m, ArH), 7.36 (1H, d of d, J 7.7Hz, J 1.4Hz, ArH), 7.53 (1H, d of d, J 7.5Hz, J 1.6Hz, ArH), 7.66 (1H, d of d, J 6.9Hz, J 1.5Hz, ArH), 7.73 (1H, d of d, J 8.7Hz, J 1.7Hz, ArH). m/z (ES$^+$) 340 (M+1)$^+$.

EXAMPLE 4

4-(Benzothiophen-2-yl)-1-(3,4-dichlorobenzyl)-1,2,3,6-tetrahydropyridine, hydrogen oxalate 4-(Benzothiophen-2-yl)-1,2,3,6-tetrahydropyridine hydrochloride (200 mg, 0.8 mmol) was reacted with 3,4-dichlorobenzyl bromide (191 mg, 0.8 mmol) as exemplified in Example 1. The crude product was triturated with hot methanol, the residual solid dissolved in dichloromethane (5 ml) and oxalic acid (33 mg, 0.37 mmol) added. The solution was concentrated in vacuo and the residual solid triturated with warm ether to afford the title compound as a white solid (150 mg, 40%) mp 263°–265° C.; (Found: C, 55.99; H, 4.24; N, 3.55. C$_{22}$H$_{19}$Cl$_2$NO$_4$S.0.5H$_2$O requires C, 55.82; H, 4.26; N, 2.96%). $\delta_H$ (DMSO-d$_6$) 2.63 (2H, m, NCH$_2$CH$_2$), 2.79 (2H, m, NCH$_2$CH$_2$), 3.21 (2H, m, NCH$_2$CH$_2$), 3.71 (2H, s, NCH$_2$Ar), 6.20 (1H, s, ArH), 7.30 (2H, m, ArH), 7.34 (2H, m, ArH), 7.60 (2H, m, ArH), 7.76 (1H, d of d, J 6.8Hz, J 2.2Hz, ArH), 7.84 (1H, d of d, J 9.2Hz, ArH). m/z (ES$^+$) 374 (M+1)$^+$.

EXAMPLE 5

4-(Benzothiophen-2-yl)-1-(4-fluorobenzyl)-1,2,3,6-tetrahydropyridine 4-(Benzothiophen-2-yl)-1,2,3,6-tetrahydropyridine hydrochloride (250 mg, 0.99 mmol) was reacted with 4-fluorobenzyl bromide (0.12 ml, 0.99 mmol) as exemplified in Example 1. The crude product was triturated with hot methanol to give the title compound as a pale yellow solid mp 142°–144° C. (Found: C, 73.78; H, 5.57; N, 4.36. C$_{20}$H$_{18}$FNS. 0.1H$_2$O requires C, 73.86; H, 5.64; N, 4.30%). $\delta_H$ (CDCl$_3$) 2.64 (2H, m, NH$_2$CH$_2$), 2.72 (2H, m, NCH$_2$CH$_2$), 3.18 (2H, m, NCH$_2$CH$_2$), 3.61 (2H, s, NCH$_2$Ar), 6.19 (1H, m, NCH$_2$CH), 7.02 (2H, t, J 8.6Hz, ArH), 7.12 (1H, s, ArH), 7.30 (4H, m, ArH), 7.67 (1H, d of d, J 6.7Hz, ArH), 7.73 (1H, d of d, J 6.8Hz, ArH). m/z (ES$^+$) 324 (M+1)$^+$.

EXAMPLE 6

4-(Benzothiophen-2-yl)-1-(4-methoxybenzyl)-1,2,3,6-tetrahydropyridine 4-(Benzothiophen-2-yl)-1,2,3,6-tetrahydropyridine hydrochloride (250 mg, 0.99 mmol) was reacted with 4-methoxybenzyl chloride (0.13 ml, 0.99 mmol) as exemplified in Example 1. The crude product was triturated with hot methanol to give the title compound as a pale yellow solid mp 158°–160° C. (Found: C, 75.09; H, 5.05; N, 4.31; C$_{21}$H$_{21}$NOS requires C, 75.19; H, 6.31; N, 4.18%). $\delta_H$ (CDCl$_3$) 2.65 (2H, m, NCH$_2$CH$_2$), 2.74 (2H, m, NCH$_2$CH$_2$), 3.20 (2H, m, NCH$_2$CH$_2$), 3.61 (2H, s, NCH$_2$Ar), 3.81 (3H, s, OMe), 6.18 (1H, m, NCH$_2$CH), 6.87 (2H, d, J 8.6Hz, ArH), 7.12 (1H, s, ArH), 7.28 (4H, m, ArH), 7.65 (1H, d, J 6.8Hz, ArH), 7.73 (1H, d, J 6.9Hz, ArH). m/z (ES$^+$) 336 (M+1)$^+$.

EXAMPLE 7

4-(Benzothiazol-2-yl)-1-benzyl-1,2,3,6-tetrahydropyridine

Step 1: 4-(Benzothiazol-2-yl)pyridine

2-Aminothiophenol (6.3 g, 0.05 mol) and 4-pyridinecarboxaldehyde (5.4 g, 0.05 mol) were dissolved in dimethylsulfoxide (35 ml) and heated until vapours distilled off at 180°–186° C. The distillation residue on cooling was partitioned between ethyl acetate and saturated ammonium chloride solution. The combined organic layers were washed with water (100 ml), dried ($MgSO_4$) and concentrated. The solid was triturated with ether to afford the title compound as a pale brown solid (9 g, 85%). $\delta_H$ ($CDCl_3$), 7.42 (1H, m, ArH), 7.51 (1H, m, ArH), 7.93 (3H, m, ArH), 8.13 (1H, d, J 8.7Hz, ArH), 8.78 (2H, m, ArH). m/z ($ES^+$) 213 $(M+1)^+$.

Step 2: 4-(Benzothiazol-2-yl)-1-benzyl-1,2,3,6-tetrahydropyridine 4-(Benzothiazol-2-yl)pyridine (4.5 g, 0.02 mol) was suspended in DMF (10 ml) and benzyl bromide (3.8 ml, 0.03 mol) added and the reaction mixture stirred at reflux for 1 hour. On cooling, the solid was filtered and washed with ether (20 ml). The solid was then suspended in ethanol (100 ml), sodium borohydride (1.05 g, 0.026 mol) added and the reaction stirred at room temperature overnight. The reaction mixture was concentrated in vacuo, the residue diluted with water (50 ml) and the product extracted into dichloromethane (3×50 ml). The combined organic layers were washed with brine, dried ($MgSO_4$), and concentrated. The crude product was purified by flash chromatography eluting with 15% ethyl acetate in petroleum ether to give a solid. Recrystallisation from ethyl acetate afforded the title compound as a white solid (4.1 g, 67%); (Found: C, 74.31; H, 5.87; N, 9.07. $C_{19}H_{18}N_2S$ requires C, 74.47; H, 5.92; N, 9.14%). $\delta_H$ ($CDCl_3$), 2.76 (2H, m, $NCH_2CH_2$), 2.83 (2H, m, $NCH_2CH_2$), 3.23 (2H, m, $NCH_2CH_2$), 3.67 (2H, s, $NCH_2Ph$), 6.67 (1H, m, $NCH_2CH$), 7.35 (7H, m, ArH), 7.81 (1H, d, J 7.9Hz, ArH), 7.97 (1H, d, J 8.1Hz, ArH). m/z ($ES^+$) 307 $(M+1)^+$.

EXAMPLE 8

4-(Benzothiazol-2-yl)-1-(4-chlorobenzyl)-1,2,3,6-tetrahydropyridine

Step 1: 4-(Benzothiazol-2-yl)-1,2,3,6-tetrahydropyridine hydrochloride 4-(Benzothiazol-2-yl)-1-benzyl-1,2,3,6-tetrahydropyridine (4 g, 0.013 mol) was debenzylated as exemplified in Example 1 step 3, to afford the title product as a pale brown solid (2.4 g, 73%). $\delta_H$ (DMSO-$d_6$) 2.92 (2H, m, $NCH_2CH_2$), 3.33 (2H, m, $NCH_2CH_2$), 3.85 (2H, m, $NCH_2CH_2$), 6.79 (1H, s, $NCH_2CH$), 7.51 (2H, m, ArH), 8.00 (1H, d, J 7.7Hz, ArH), 8.10 (1H, d, J 7.6Hz, ArH), 9.63 (1H, br s, NH). m/z ($ES^+$) 217 $(M+1)^+$.

Step 2: 4-(Benzothiazol-2-yl)-1-(4-chlorobenzyl)-1,2,3,6-tetrahydropyridine 4-(Benzothiazol-2-yl)-1,2,3,6-tetrahydropyridine hydrochloride (520 mg, 2 mmol) was reacted with 4-chlorobenzyl bromide (507 mg, 2.4 mmol) as exemplified in Example 1. The crude product was recrystallised from dichloromethane and methanol to afford the title compound as a yellow solid (410 mg, 60%); (Found: C, 66.70; H, 4.87; N, 8.16. $C_{19}H_{17}ClN_2S$ requires C, 66.95; H, 5.03; N, 8.22%). $\delta_H$ ($CDCl_3$), 2.74 (2H, m, $NCH_2CH_2$), 2.83 (2H, m, $NCH_2CH_2$), 3.22 (2H, m, $NCH_2CH_2$), 3.63 (2H, s, $NCH_2Ar$), 6.67 (1H, m, $NCH_2CH$), 7.31 (4H, s, ArH), 7.34 (1H, d of t, J 8.1Hz, J 1.2Hz, ArH), 7.44 (1H, d of t, J 7.4Hz, J 1.2Hz, ArH), 7.82 (1H, d, J 7.8Hz, ArH), 7.97 (1H, d, J 8.1Hz, ArH). m/z ($ES^+$) 341 $(M+1)^+$.

EXAMPLE 9

4-(Benzothiazol-2-yl)-1-(3-chlorobenzyl)-1,2,3,6-tetrahydropyridine 4-(Benzothiazol-2-yl)-1,2,3,6-tetrahydropyridine hydrochloride (200 mg, 0.8 mmol) was reacted with 3-chlorobenzyl bromide (0.1 ml, 0.8 mmol) as exemplified in Example 1. The crude product was purified by flash chromatography eluting with 15% ethyl acetate in petroleum ether to give the title compound as a pale yellow solid (120 mg, 45%); (Found: C, 65.57; H, 4.87; N, 7.59. $C_{19}H_{17}ClNS \cdot 0.5H_2O$ requires C, 65.22; H, 5.19; N, 8.01%). $\delta_H$ ($CDCl_3$), 2.77 (2H, m, $NCH_2CH_2$), 2.84 (2H, m, $NCH_2CH_2$), 3.24 (2H, m, $NCH_2CH_2$), 3.65 (2H, s, $NCH_2Ar$), 6.68 (1H, m, $NCH_2CH$), 7.25 (2H, s, ArH), 7.36 (4H, m, ArH), 7.82 (1H, d, J 8.0Hz, ArH), 7.98 (1H, d, J 8.1Hz, ArH). m/z ($ES^+$) 341 $(M+1)^+$.

EXAMPLE 10

4-(Benzothiazol-2-yl)-1-(2-chlorobenzyl)-1,2,3,6-tetrahydropyridine 4-(Benzothiazol-2-yl)-1,2,3,6-tetrahydropyridine hydrochloride (200 mg, 0.8 mmol) was reacted with 2-chlorobenzyl bromide (0.13 ml, 0.8 mmol) as exemplified in Example 1. The crude product was purified by flash chromatography eluting with 15% ethyl acetate in petroleum ether to give the title compound as a yellow solid (120 mg, 44%). (Found: C, 65.13; H, 4.72; N, 7.33. $C_{19}H_{17}ClN_2S \cdot 0.5H_2O$ requires C, 65.22; H, 5.19; N, 8.01%). $\delta_H$ ($CDCl_3$), 2.84 (4H, m, $CH_2$), 3.33 (2H, m, $NCH_2CH_2$), 3.80 (2H, s, $NCH_2Ar$), 6.70 (1H, m, $NCH_2CH$), 7.41 (6H, m, ArH), 7.82 (1H, d, J 7.8Hz, ArH), 7.98 (1H, d, J 8.1Hz, ArH). m/z ($ES^+$) 341 $(M+1)^+$.

EXAMPLE 11

4-(Benzothiazol-2-yl)-1-(4-cyanobenzyl)-1,2,3,6-tetrahydropyridine 4-(Benzothiazol-2-yl)-1,2,3,6-tetrahydropyridine hydrochloride (300 mg, 1.2 mmol) was reacted with α-bromo-p-tolunitrile (280 mg, 1.44 mmol) as exemplified in Example 1. The crude product was purified by flash chromatography eluting with 25% ethyl acetate in petroleum spirit to give a solid. Recrystallisation of this solid from ethyl acetate yielded the title compound as a yellow solid (240 mg, 60%) mp. 165°–166° C. (Found: C, 72.00; H, 4.92; N, 12.61. $C_{20}H_{17}N_3S$ requires C, 72.48; H, 5.17; N, 12.68%). $\delta_H$ ($CDCl_3$), 2.76 (2H, m, $NCH_2CH_2$), 2.83 (2H, m, $NCH_2CH_2$), 3.24 (2H, m, $NCH_2CH_2$), 3.72 (2H, s, $NCH_2Ar$), 6.68 (1H, m, $NCH_2CH$), 7.41 (4H, m, ArH), 7.51 (1H, d, J 8.4Hz, ArH), 7.64 (1H, d, J 8.4Hz, ArH), 7.83 (1H, d, J 7.0Hz, ArH), 8.00 (1H, d, J 8.3Hz, ArH). m/z ($ES^+$) 332 $(M+1)^+$.

EXAMPLE 12

1-Benzyl-4-(5-chlorobenzothiazol-2-yl)-1,2,3,6-tetrahydropyridine

Step 1: 4-(5-Chlorobenzothiazol-2-yl)pyridine

2-Amino-4-chlorothiophenol (6.5 g, 0.04 mol) and 4-pyridine carboxaldehyde (4.4. g, 0.04 mol) were reacted as exemplified in Example 7 step 1, to afford the title compound as a brown solid (1.8 g, 20%). $\delta_H$ (CDCl$_3$), 7.44 (1H, m, ArH), 7.86 (1H, m, ArH), 7.92 (2H, m, ArH), 8.08 (1H, s, ArH), 8.78 (2H, m, ArH). m/z (ES$^+$) 247 (M+1)$^+$.

Step 2: 1-Benzyl-4-(5-chlorobenzothiazol-2-yl)-1,2,3,6-tetrahydropyridine 4-(5-Chlorobenzothiazol-2-yl)pyridine (1.8 g, 7.3 mmol) was reacted with benzyl bromide (1.3 ml, 10.95 mmol), followed by sodium borohydride (361 mg, 9.5 mmol) as exemplified in Example 7 step 2. The crude product was purified by flash chromatography eluting with 15% ethyl acetate in petroleum ether to give a solid. Recrystallisation from ethyl acetate afforded the title compound as a pale yellow solid (1.63 g, 66%); (Found: C, 66.83; H, 5.00; N, 8.20. C$_{19}$H$_{17}$ClN$_2$S requires C, 66.95; H, 5.03; N, 8.22%). $\delta_H$ (CDCl$_3$), 2.76 (4H, m, CH$_2$), 3.24 (2H, m, CH$_2$), 3.67 (2H, s, NCH$_2$Ar), 6.70 (1H, m, NCH$_2$CH), 7.32 (5H, m, ArH), 7.71 (1H, d, J 8.5Hz, ArH), 7.95 (1H, d, J 1.9Hz, ArH). m/z (ES$^+$) 341 (M+1)$^+$.

EXAMPLE 13

4-(5-Chlorobenzothiazol-2-yl)-1-(4-chlorobenzyl)-1,2,3,6-tetrahydropyridine, hydrogen oxalate Step 1: 4-(5-Chlorobenzothiazol-2-yl)-1,2,3,6-tetrahydropyridine hydrochloride 1-Benzyl-4-(5-chlorobenzothiazol-1,2,3,6-tetrahydropyridine (1.56 g, 4.6 mmol) was debenzylated as exemplified in Example 1 step 3, to afford the title product as a yellow solid (1 g, 76%). $\delta_H$ (DMSO-d$_6$) 2.90 (2H, m, NCH$_2$CH$_2$), 3.17 (2H, s, NCH$_2$CH$_2$), 3.86 (2H, m, NCH$_2$CH$_2$), 6.84 (1H, m, NCH$_2$CH), 7.52 (1H, d of d, J 8.6Hz, J 2.1Hz, ArH), 8.09 (1H, d, J 2Hz, ArH), 8.15 (1H, d, J 8.6Hz, ArH), 9.48 (1H, br s, NH); m/z (ES$^+$) 375 (M+1)$^+$.

Step 2: 4-(5-Chlorobenzothiazol-2-yl)-1-(4-chlorobenzyl)-1,2,3,6-tetrahydropyridine oxalate 4-(5-Chlorobenzothiazol-2-yl)-1,2,3,6-tetrahydropyridine hydrochloride (150 mg, 0.5mmol) was reacted with 4-chlorobenzyl bromide (107 mg, 0.5 mmol) as exemplified in Example 1. The crude product was purified by flash chromatography eluting with 15% ethyl acetate in petroleum ether to give an orange oil (50 mg). The product was dissolved in dichloromethane (5 ml) and oxalic acid (12 mg) added. The solution was concentrated in vacuo and the residual solid triturated with warm ethyl acetate to afford the title compound as a pale yellow solid (30 mg, 12%) m.p. 226°–228° C.; (Found: C, 53.23; H, 3.58; N, 6.24. C$_{21.2}$H$_{18.2}$Cl$_2$N$_2$O$_{4.4}$S requires C, 53.68; H, 3.87; N, 5.91%) $\delta_H$ (DMSO-d$_6$) 2.73 (2H, m, NCH$_2$CH$_2$), 2.82 (2H, m, NCH$_2$CH$_2$), 3.31 (2H, m, NCH$_2$CH$_2$), 3.76 (2H, s, NCH$_2$Ar), 6.78 (1H, m, NCH$_2$CH), 7.42 (5H, m, ArH), 7.98 (1H, d, J 2Hz, ArH), 8.05 (1H, d, J 8.5Hz, ArH); m/z (ES$^+$) 375 (M+1)$^+$.

EXAMPLE 14

4-(5-Chlorobenzothiazol-2-yl)-1-(3-chlorobenzyl)-1,2,3,6-tetrahydropyridine, hydrogen oxalate 4-(5-Chlorobenzothiazol-2-yl)-1,2,3,6-tetrahydropyridine hydrochloride (150 mg, 0.5 mmol) was reacted with 3-chlorobenzyl bromide (0.07 ml, 0.5 mmol) as exemplified in Example 1. The crude product was purified by flash chromatography eluting with 15% ethyl acetate in petroleum ether to give an orange solid (80 mg, 41%). The product was dissolved in dichloromethane (5 ml) and oxalic acid (19 mg) was added. The solution was concentrated in vacuo and the residual solid triturated with warm ether to afford the title compound as a yellow solid. (Found C, 54.01; H, 3.85; N, 5.97. C$_{21}$H$_{18}$Cl$_2$N$_2$O$_4$S requires C, 54.20; H, 3.90; N, 6.02%). $\delta_H$ (DMSO-d$_6$) 2.72 (2H, m, NCH$_2$CH$_2$), 2.81 (2H, s, NCH$_2$CH$_2$), 3.30 (2H, m, NCH$_2$CH$_2$), 3.75 (2H, s, NCH$_2$Ar), 6.79 (1H, m, NCH$_2$CH), 7.39 (5H, m, ArH), 7.99 (1H, s, ArH), 8.05 (1H, d, J 8.7Hz, ArH); m/z (ES$^+$) 375 (M+1)$^+$.

EXAMPLE 15

4-(5-Chlorobenzothiazol-2-yl)-1-(2-chlorobenzyl)-1,2,3,6-tetrahydropyridine, hydrogen oxalate 4-(5-Chlorobenzothiazol-2-yl)-1,2,3,6-tetrahydropyridine hydrochloride (150 mg, 0.5 mmol) was reacted with 2-chlorobenzyl bromide (0.08 ml, 0.5 mmol) as exemplified in Example 1. The crude product was purified by flash chromatography eluting with 10% ethyl acetate in petroleum ether to give an orange solid (90 mg). The product was dissolved in dichloromethane (5 ml) and oxalic acid (22 mg) was added. The solution was concentrated in vacuo and the residual solid triturated with hot ethyl acetate to afford the title compound as a white solid (60 mg, 25%); mp. 205°–208° C. (Found C, 53.82; H, 3.72; N, 6.66. C$_{21}$H$_{18}$Cl$_2$N$_2$O$_4$S requires C, 54.2; H, 3.90; N, 6.02%). $\delta_H$ (DMSO-d$_6$) 2.71 (2H, m, NCH$_2$CH$_2$), 2.83 (2H, m, NCH$_2$CH$_2$), 3.33 (2H, m, NCH$_2$CH$_2$), 3.81 (2H, s, NCH$_2$Ar), 6.79 (1H, m, NCH$_2$CH), 7.32 (2H, m, ArH), 7.43 (2H, m, ArH), 7.53 (1H, m, ArH), 7.98 (1H, d, J 2Hz, ArH), 8.04 (1H, d, J 8.6Hz, ArH); m/z (ES$^+$) 375 (M+1)$^+$.

EXAMPLE 16

1-Benzyl-4-(5-trifluoromethylbenzothiazol-2-yl)-1,2,3,6-tetrahydropyridine

Step 1: 4-(5-Trifluoromethylbenzothiazol-2-yl)pyridine

3-Amino-4-mercaptobenzotrifluoride (8.5 g, 0.04 mol) and 4-pyridine carboxaldehyde (4.2 ml, 0.04 mol) were reacted as exemplified in Example 7 step 1, to afford the title compound as a brown solid (10 g, 89%). $\delta_H$ (CDCl$_3$), 7.69 (1H, d of d, J 8.4Hz, J 1.7Hz, ArH), 7.93 (2H, m, ArH), 8.06 (1H, d, J 8.4Hz, ArH), 8.40 (1H, d, J 0.7Hz, ArH), 8.81 (2H, m, ArH). m/z (ES$^+$) 281 (M+1)$^+$.

Step 2: 1-Benzyl-4-(5-trifluoromethylbenzothiazol-2-yl)-1,2,3,6-tetrahydropyridine 4-(5-Trifluoromethylbenzothiazol-2-yl)pyridine (10 g, 0.04 mol) was reacted with benzyl bromide (6.4 ml, 0.06 mol) followed by sodium borohydride (1.76 g, 0.052 mol) as exemplified in Example 7 step 2. The crude product was purified by flash chromatography eluting with 15% ethyl acetate in petroleum ether to give a yellow solid. Recrystallisation from ethyl acetate afforded the title compound as a pale yellow solid (7 g, 47%); mp. 124°–125° C.; (Found: C, 63.85; H, 4.48; N, 7.48. C$_{20}$H$_{17}$F$_3$N$_2$S requires C, 64.16; H, 4.58; N, 7.48%). $\delta_H$ (CDCl$_3$), 2.75 (2H, m, NCH$_2$CH$_2$), 2.81 (2H, m, NCH$_2$CH$_2$), 3.24 (2H, m, NCH$_2$CH$_2$), 3.67 (2H, s, NCH$_2$Ar), 6.71 (1H, m, NCH$_2$CH), 7.28 (5H, m, ArH), 7.55 (1H, d of d, J 8.4Hz, J 1.4Hz, ArH), 7.89 (1H, d, J 8.4Hz, ArH), 8.23 (1H, s, ArH); m/z (ES$^+$) 375 (M+1)$^+$.

EXAMPLE 17

4-(Benzoxazol-2-yl)-1-benzyl-1,2,3,6-tetrahydropyridine. Hydrogen oxalate

Step 1: 4-(Benzoxazol-2-yl)pyridine

A mixture of 2-aminophenol (10.9 g, 100 mmol), isonicotinic acid (12.3 g, 100 mmol) and boric acid (6.1 g, 100 mmol) in xylene (500 ml) was heated at reflux, under a nitrogen atmosphere, for 17 hours. The mixture was cooled to room temperature and the orange suspension partitioned between sodium hydroxide solution (4N, 500 ml) and ethyl acetate (500 ml), the phases were separated and the organic layer washed with sodium hydroxide solution (2N, 2×300 ml), water (100 ml) and brine (100 ml).

Organics were dried over magnesium sulphate and evaporated in vacuo to give the title compound as an orange solid (2.1 g, 11%); $\delta_H$ (CDCl$_3$), 7.40–7.44 (2H, m, ArH), 7.62–7.64 (1H, m, ArH), 7.81–7.84 (1H, m, ArH), 8.09 (2H, dd, J 4.6, 1.4Hz, pyridyl CH$_2$) and 8.82–8.83 (2H, m, ArH); m/z (ES$^+$) 197 (M+1)$^+$.

Step 2: 4-(Benzoxazol-2-yl)-1-benzyl-1,2,3,6-tetrahydropyridine hydrogen oxalate Benzyl bromide (1.4 ml, 11.8 mmol) was added to a solution of 4-(benzoxazol-2-yl)piperidine (2.0 g, 10.2 mmol) in DMF (5 ml), under a nitrogen atmosphere, and the resultant suspension stirred at 100°–120° C. for 1½ hours. The mixture was cooled to room temperature, diluted with ethanol (5 ml) and the yellow solid collected by filtration and washed with ethanol (1×5 ml and 1×2 ml).

The quaternary salt was suspended in ethanol under a nitrogen atmosphere, sodium borohydride (506 mg, 13.3 mmol) added portionwise and the mixture stirred at room temperature for 2 hours after which the mixture was evaporated in vacuo. The residue was partitioned between water (40 ml) and ethyl acetate (40 ml), the solids present were removed by filtration. The phases were separated and the aqueous extracted with ethyl acetate (2×40ml). The combined organics were washed with brine (20 ml), dried over magnesium sulfate and evaporated in vacuo to a yellow solid (1.5 g).

A portion of this material (250 mg, 0.86 mmol) was treated with oxalic acid (77 mg, 0.86 mmol) in ether. The fine suspension was evaporated in vacuo and the residue recrystallised from methanol to furnish the title compound as a white solid (87 mg, 57%), mp.>230° C. dec; (Found: C, 66.93; H, 5.17; N, 7.33. C$_{19}$H$_{18}$N$_2$O. (CO$_2$H)$_2$ requires C, 66.31; H, 5.30; N, 7.36%); $\delta_H$ (DMSO-d$_6$), 2.75 (2H, m, tetrahydropyridinyl CH$_2$), 2.98–2.99 (2H, m, tetrahydropyridinyl CH$_2$), 3.49 (2H, m, tetrahydropyridinyl CH$_2$), 6.96 (1H, s, tetrahydropyridinyl CH), 7.34–7.45 (7H, m, ArH) and 7.69–7.75 (2H, m, ArH); m/z (ES$^+$) 291 (M+1)$^+$.

Prepared in an analogous manner were:

EXAMPLE 18

4-(5-Chlorobenzoxazol-2-yl)-1-benzyl-1,2,3,6-tetrahydropyridine hydrogen Oxalate Mp. 215°–217° C. (Methanol); (Found: C, 60.74; H, 4.29; N, 6.80. C$_{19}$H$_{17}$ClN$_2$O. (CO$_2$H)$_2$ requires C, 60.80; H, 4.62; N, 6.75%); $\delta_H$ (DMSO-d$_6$) 2.71 (2H, br s, tetrahydropyridinyl CH$_2$), 2.95 (2H, m, tetrahydropyridinyl CH$_2$), 3.46 (2H, br s, tetrahydropyridinyl CH$_2$), 3.93 (2H, s, NCH$_2$Ar), 7.00 (1H, br s, tetrahydropyridinyl CH), 7.35–7.45 (6H, m, ArH), 7.74 (1H, d, J 8.7Hz, 7'H) and 7.85 (1H, d, J 2.1Hz, 4'H); m/z (ES$^+$) 325 (M+1)$^+$.

EXAMPLE 19

4-(5-Chlorobenzoxazol-2-yl)-1-(3-chlorobenzyl)-1,2,3,6-tetrahydropyridine

Mp. 117°–118° C.; $\delta_H$ (CDCl$_3$), 2.75 (4H, s, CH$_2$), 3.26 (2H, d, J 3.5Hz, CH$_2$), 3.64 (2H, s, ArCH$_2$), 6.98 (1H, m, CH), 7.27 (4H, m, ArH), 7.38 (2H, s, ArH), 7.67 (1H, s, ArH); m/z (ES$^+$) 359 (M+1)$^+$.

EXAMPLE 20

4-(5-Chlorobenzoxazol-2-yl)-1-(4-chlorobenzyl)-1,2,3,6-tetrahydropyridine

Mp. 145° C.; $\delta_H$ (CDCl$_3$), 2.74 (4H, s, CH$_2$), 3.25 (2H, s, CH$_2$), 3.63 (2H, s, ArCH$_2$), 6.97 (1H, m, CH), 7.27 (5H, m, ArH), 7.39 (1H, d, J 8.65Hz, ArH), 7.66 (1H, s, ArH); m/z (ES$^+$) 359 (M+1)$^+$.

EXAMPLE 21

4-(5-Chlorobenzoxazol-2-yl)-1-(4-fluorobenzyl)-1,2,3,6-tetrahydropyridine

Mp. 153°–155° C.; Found: C, 66.21; H, 4.61; N, 8.29. C$_{19}$H$_{16}$ClFN$_2$O requires C, 66.57; H, 4.71; N, 8.17%. $\delta_H$ (CDCl$_3$), 2.74 (4H, s, CH$_2$), 3.24 (2H, s, CH$_2$), 3.63 (2H, s, ArCH$_2$), 7.00 (3H, m), 7.26–7.41 (4H, m), 7.66 (1H, s, ArH); m/z (ES$^+$) 343 (M+1)$^+$.

EXAMPLE 22

4-(5-Chlorobenzoxazol-2-yl)-1-(4-methylbenzyl)-1,2,3,6-tetrahydropyridine

Mp. 105° C.; Found: C, 69.25; H, 5.23; N, 8.24. C$_{20}$H$_{19}$ClN$_2$O requires C, 69.78; H, 5.74; N, 8.14%. $\delta_H$ (CDCl$_3$), 2.36 (3H, s, CH$_3$), 2.75 (4H, s, CH$_2$), 3.27 (2H, br s, CH$_2$), 3.65 (2H, s, ArCH$_2$), 6.99 (1H, m, CH), 7.14 (1H, S, ArH), 7.17 (1H, s, ArH), 7.25–7.29 (3H, m, ArH), 7.38 (1H, s, AH), 7.66 (1H, s, ArH); m/z (ES$^+$) 399 (+1)$^+$.

EXAMPLE 23

4-(5-Chlorobenzoxazol-2-yl)-1-(4-methoxybenzyl)-1,2,3,6-tetrahydropyridine

Mp. 110°–111° C.; Found: C, 67.51; H, 4.82; N, 8.05. C$_{20}$H$_{19}$ClN$_2$O$_2$ requires C, 67.70; H, 5.39; N, 7.90%. $\delta_H$ (CDCl$_3$), 2.74 (4H, s, CH$_2$), 3.24 (2H, d, J 3.5Hz, CH$_2$), 3.61 (2H, s, ArCH$_2$), 3.82 (3H, s, OCH$_3$), 6.87 (2H, m, ArH), 6.98 (1H, m, CH), 7.28 (3H, m, ArH), 7.37 (1H, s, ArH), 7.66 (1H, s, ArH); m/z (ES$^+$) 355 (M+1)$^+$.

EXAMPLE 24

1-Benzyl-4-(6-methylbenzoxazol-2-yl)-1,2,3,6-tetrahydropyridine

Mp. 134° C.; $\delta_H$ (CDCl$_3$), 2.47 (3H, s, CH$_3$), 2.75 (4H, s, CH$_2$), 3.25 (2H, d, J 3.4Hz, CH$_2$), 3.67 (2H, s, ArCH$_2$), 6.92 (1H, m, CH), 7.11 (1H, d, J 7.92Hz, ArH), 7.26–7.39 (6H, m, ArH), 7.55 (1H, d, J 8.1Hz, ArH); m/z (ES$^+$) 305 (M+1)$^+$.

EXAMPLE 25

1-Benzyl-4-(4-methylbenzoxazol-2-yl)-1,2,3,6-tetrahydropyridine

Mp. 185°–187° C.; Found: C, 67.02; H, 6.01; N, 8.10. C$_{20}$H$_{21}$ClN$_2$O. 0.85H$_2$O requires C, 67.44; H, 6.42; N, 7.87%. $\delta_H$ (CDCl$_3$), 2.61 (3H, s, CH$_3$), 2.75 (4H, br s, CH$_2$), 3.25 (2H, m, CH$_2$), 3.68 (2H, s, ArCH$_2$), 6.94 (1H, m, CH), 7.13–7.40 (8H, m, ArH); m/z (ES$^+$) 305 (M+1)$^+$.

EXAMPLE 26

1-Benzyl-4-(5-methylbenzoxazol-2-yl)-1,2,3,6-tetrahydropyridine

Mp. 120° C.; Found: C, 78.74; H, 6.39; N, 9.16. C$_{20}$H$_{20}$N$_2$O requires C, 78.92; H, 6.62; N, 9.20%. $^1$H NMR (250MHz, CDCl$_3$) δ 2.45 (3H, s, CH$_3$), 2.76 (4H, s, CH$_2$), 3.26 (2H, d, J 3.5Hz, CH$_2$), 3.68 (2H, s, ArCH$_2$), 6.94 (1H, m, CH), 7.11 (1H, m, ArH), 7.26–7.40 (6H, m, ArH), 7.48 (1H, s, ArH).

EXAMPLE 27

1-Benzyl-4-(benzimidazol-2-yl)-1,2,3,6-tetrahydropyridine

Step 1: 2-(4'-Pyridyl)benzimidazole 1,2-Phenylenediamine (5 g, 46.2 mmol), isonicotinic acid (4.07 g, 33 mmol) and trimethylpolyphosphate in 1,2-dichlorobenzene (100 ml) were heated to 190° C. for 2 hours. On cooling the solution was partitioned between sodium hydroxide (2N) and dichloromethane, the aqueous layer separated, reacidified to pH 6 (2M HCl), and the precipitate filtered. The remaining solid in the organic phase was filtered, dissolved in sodium hydroxide (2N), reacidified and filtered to yield further product, giving a total yield of 5.0 g (78%); δ$_H$ (DMSO-d$_6$) 7.27 (2H, m, ArH), 7.67 (2H, m, ArH), 8.11 (2H, m, ArH), 8.79 (2H, m, ArH).

Step 2: 1-Benzyl-4-(benzimidazol-2-yl)-1,2,3,6-tetrahydropyridine

The above benzimidazole (1.74 g, 8.92 mmol) and benzyl bromide (2.33 ml, 19.62 mmol) in DMF (7 ml) were heated to 120° C. for 2 hours. On cooling the resulting solid was collected, washed with cold ethanol and dried to yield 1 g (31%) of the quaternary salt. The salt (1 g, 2.73 mmol) and sodium borohydride (135 mg, 3.55 mmol) in ethanol (20 ml) were stirred at room temperature overnight. A further 54 mg (0.4 eq) of sodium borohydride was added and the reaction stirred for 1 hour. The suspension was evaporated to dryness, added to ethyl acetate, washed with three portions of water, dried (MgSO$_4$) and evaporated. The residue was purified on silica eluting with methanol in dichloromethane to yield 370 mg (47%) of the title compound. This was recrystallised from ethyl acetate and petroleum ether; (Found: C, 78.21; H, 6.47;N, 14.20. C$_{19}$H$_{18}$N$_3$. 0.2H$_2$O requires C, 77.89; H. 6.67;N, 14.34%); δ$_H$ (CDCl$_3$) 2.77 (4H, m, tetrahydropyridinyl CH$_2$), 3.23 (2H, m, tetrahydropyridinyl CH$_2$), 3.68 (2H, s, NCH$_2$Ph), 6.54 (1H, m, C=CHCH$_2$), 7.21–7.39 (9H, m, ArH/PhH); m/z 290 (M+1)$^+$.

Prepared analogously were:

EXAMPLE 28

4-(Benzimidazol-2-yl)-1-(4-cyanobenzyl)-1,2,3,6-tetrahydropyridine, bis(hydrogen oxalate)

(Found: C, 58.57; H, 4.57;N, 11.75. C$_{24}$H$_{22}$N$_4$O$_8$ requires C, 5.8.30; H, 4.45;N, 11.34%); δ$_H$ DMSO-d$_6$) 2.78 (2H, m, tetrahydropyridinyl CH$_2$), 2.98 (2H, m, tetrahydropyridinyl CH$_2$), 3.46 (2H, m, tetrahydropyridinyl CH$_2$), 4.04 (2H, s, NCH$_2$Ar), 6.71 (1H, m, C=CHCH$_2$), 7.17 (2H, m, ArH), 7.52 (2H, m, ArH), 7.65 (2H, d, J 8.01Hz, ArH), 7.89 (2H, d, J 8.07Hz, ArH); m/z 315 (M+1)$^+$.

EXAMPLE 29

4-(Benzimidazol-2-yl)-1-(4-bromobenzyl)-1,2,3,6-tetrahydropyridine (Found: C, 60.09; H, 5.37;N, 10.66. C$_{19}$H$_{18}$N$_3$Br. 0.5H$_2$O requires C, 60.33; H, 5.33;N, 11.11%); δ$_H$ (DMSO-d$_6$) 2.65 (4H, m, tetrahydropyridinyl CH$_2$), 3.16 (2H, m, tetrahydropyridinyl CH$_2$), 3.60 (2H, s, NCH$_2$Ar), 6.69 (1H, m, C=CHCH$_2$), 7.11–7.19 (2H, m, ArH), 7.32 (2H, d, J 8.36Hz, ArH), 7.42 (1H, d, J 7.13Hz, ArH), 7.52–7.58 (3H, m, ArH); m/z 368, 370 (M+1)$^+$.

EXAMPLE 30

4-(Benzimidazol-2-yl)-1-(4-methoxybenzyl)-1,2,3,6-tetrahydropyridine (Found: C, 74.33; H, 6.33;N, 13.41. C$_{20}$H$_{21}$N$_3$O 0.1H$_2$O requires C, 74.64; H, 6.58;N, 13.06%); δ$_H$ (DMSO-d$_6$) 2.63 (4H, m, tetrahydropyridinyl CH$_2$), 3.13 (2H, m, tetrahydropyridinyl CH$_2$), 3.55 (2H, s, NCH$_2$Ar), 3.75 (3H, s, ArOCH$_3$), 6.69 (1H, m, C=CHCH$_2$), 6.90 (2H, d, J 8.66Hz, ArH), 7.14 (2H, m, ArH), 7.42 (1H, m, J 7.33Hz, ArH), 7.56 (1H, m, J 6.69Hz, ArH), 7.76 (2H, d, J 8.60Hz, ArH); m/z 320 (M+1)$^+$.

EXAMPLE 31

4-(Benzimidazol-2-yl)-1-(3,4-dichlorobenzyl)-1,2,3,6-tetrahydropyridine (Found: C, 63.84; H, 4.63;N, 11.61. C$_{19}$H$_{17}$N$_3$Cl$_2$ requires C, 63.69; H, 4.75;N, 11.73%); δ$_H$ (DMSO-d$_6$) 2.66 (4H, m, tetrahydropyridinyl CH$_2$), 3.17 (2H, m, tetrahydropyridinyl CH$_2$), 3.63 (2H, s, NCH$_2$Ar), 7.09–7.17 (2H, m, ArH), 7.35–7.44 (2H, m, ArH), 7.56–7.62 (3H, m, ArH); m/z 358 (M+1).

EXAMPLE 32

4-(Benzimidazol-2-yl)-1-(4-chlorobenzyl)-1,2,3,6-tetrahydropyridine, bis(hydrogen oxalate)

(Found: C, 54.40; H, 3.10;N, 8.20. C$_{23}$H$_{22}$N$_3$ClO$_8$ requires C, 54.90; H, 4.37;N, 8.35%); δ$_H$ (CDCl$_3$) 2.76 (4H, m, tetrahydropyridinyl CH$_2$), 3.19 (2H, m, tetrahydropyridinyl CH$_2$), 3.62 (2H, s, NCH$_2$Ar), 6.54 (1H, m, C=CHCH$_2$), 7.20–7.31 (6H, m, ArH), 7.39 (1H, m, ArH), 7.73 (1H, m, ArH); m/z 324 (M+1)$^+$.

EXAMPLE 33

1-(4-Chlorobenzyl)-4-(4-methylbenzimidazol-2-yl)-1,2,3,6-tetrahydropyridine (Found: C, 57.41; H, 5.47;N, 9.59. C$_{20}$H$_{22}$N$_3$Cl$_2$ 0.55H$_2$O requires C, 57.10; H, 5.54;N, 9.98%) δ$_H$ (D$_2$O) 2.59 (3H, s, ArCH$_3$), 3.07 (2H, br s, tetrahydropyridinyl CH$_2$), 3.35 (2H, s, tetrahydropyridinyl CH$_2$), 4.13 (2H, m, tetrahydropyridinyl CH$_2$), 4.53 (2H, s, NCH$_2$Ar), 6.98 (1H, br s, C=CHCH$_2$), 7.35 (1H, d, J 7.35Hz, ArH), 7.46 (1H, t, J 7.49Hz, ArH), 7.54–7.59 (5H, m, ArH); m/z 338 (M+1)$^+$.

EXAMPLE 34

1-(4-Chlorobenzyl)-4-(4,5-dimethylbenzimidazol-2-yl)-1,2,3,6-tetrahydropyridine (Found: C, 68.14; H, 6.51;N, 11.29. C$_{21}$H$_{22}$N$_3$Cl. H$_2$O requires C, 68.19; H, 6.54;N, 11.36%); δ$_H$ (CDCl$_3$) 2.37 (3H, s, ArCH$_3$), 2.46 (3H, s, ArCH$_3$), 2.73–2.77 (4H, m, tetrahydropyridinyl CH$_2$), 3.17 (2H, m, tetrahydropyridinyl CH$_2$), 3.62 (2H, s, NCH$_2$Ar), 6.53 (1H, m, C=CHCH$_2$), 7.03 (1H, d, J 8.19Hz, ArH), 7.30 (5H, m, ArH); m/z 352 (M+1)$^+$.

EXAMPLE 35

1-Benzyl-4-(5-chlorobenzimidazol-2-yl)-1,2,3,6-tetrahydropyridine, bis(hydrogen oxalate)

Step 1: 5-Chloro-2-(4'-pyridyl)benzimidazole
4-Chloro-1,2-phenylenediamine (7.13 g, 0.05 mol) and 4-pyridine carboxaldehyde (4.8 ml, 0.05 mol) in DMSO (35 ml) were heated to 200° C. for 45 minutes. On cooling to room temperature the mixture was partitioned between ethyl acetate and saturated ammonium chloride, the organic layer washed with ammonium chloride and brine, and dried (MgSO$_4$). On evaporation to dryness the resulting red solid was triturated in ether, yield 5.61 g (49%).

Step 2: 1-Benzyl-4-(5-chlorobenzimidazol-2-yl)-1,2,3,6-tetrahydropyridine, bis(hydrogen oxalate)

The above compound was prepared as in Example 27, step 2. (Found: C, 54.80; H, 4.12;N, 8.12. C$_{23}$H$_{23}$N$_3$ClO$_8$ requires C, 54.71; H, 4.59;N, 8.32%); $\delta_H$ (CDCl$_3$) 7.15–7.47 (8H, m, ArH), 6.53 (1H, m, C=CHCH$_2$), 3.67 (2H, s, NCH$_2$Ph), 3.18 (2H, m, tetrahydropyridinyl CH$_2$), 2.76 (4H, m, tetrahydropyridinyl CH$_2$); m/z 324 (M+1)$^+$.

Prepared analogously were:

EXAMPLE 36

4-(5-Chlorobenzimidazol-2-yl)-1-(4-chlorobenzyl)-1,2,3,6-tetrahydropyridine, bis(hydrogen oxalate)

(Found: C, 50.15; H, 3.65;N, 7.71. C$_{23}$H$_{21}$N$_3$Cl$_2$O$_8$ 0.5H$_2$O requires C, 50.47; H, 4.05;N, 7.68%); $\delta_H$ (DMSO-d$_6$) 2.82 (2H, m, tetrahydropyridinyl CH$_2$), 3.15 (2H, m, tetrahydropyridinyl CH$_2$), 3.62 (2H, m, tetrahydropyridinyl CH$_2$), 4.13 (2H, s, NCH$_2$Ar), 6.72 (1H, m, C=CHCH$_2$), 7.19 (1H, m, ArH), 7.48–7.59 (6H, m, ArH); m/z 358 (M+1)$^+$.

EXAMPLE 37

4-(5-Chlorobenzimidazol-2-yl)-1-(3-chlorobenzyl)-1,2,3,6-tetrahydropyridine, bis(hydrogen oxalate)

(Found: C, 48.65; H, 4.07;N, 8.58. C$_{23}$H$_{21}$N$_3$Cl$_2$O$_8$ 1.5H$_2$O requires C, 48.46; H, 4.28;N, 7.43%). $\delta_H$ (DMSO-d$_6$) 2.81 (2H, m, tetrahydropyridinyl CH$_2$), 3.11 (2H, m, tetrahydropyridinyl CH$_3$), 3.59 (2H, m, tetrahydropyridinyl CH$_3$), 4.09 (2H, s, NCH$_2$Ar), 6.73 (1H, m, C=CHCH$_2$), 7.17–7.22 (1H, m, ArH), 7.47–7.59 (6H, m, ArH); m/z 358 (M+1)$^+$.

EXAMPLE 38

4-(5-Chlorobenzimidazol-2-yl)-1-(2-chlorobenzyl)-1,2,3,6-tetrahydropyridine, bis(hydrogen oxalate)

(Found: C, 50.97; H, 3.67;N, 7.95. C$_{23}$H$_{21}$N$_3$Cl$_2$O$_8$ requires C, 51.31; H, 3.91;N, 7.82%). $\delta_H$ (DMSO-d$_6$) 2.81 (2H, m, tetrahydropyridinyl CH$_2$), 3.13 (2H, m, tetrahydropyridinyl CH$_2$), 3.61 (2H, m, tetrahydropyridinyl CH$_2$), 4.12 (2H, s, CH$_2$Ar), 6.72 (1H, m, C=CHCH$_2$), 7.17–7.21 (1H, m, ArH), 7.49–7.59 (6H, m, ArH). m/z 358 (M+1)$^+$.

EXAMPLE 39

1-(3-Chlorobenzyl)-4-(5-trifluoromethylbenzimidazol-2-yl)-1,2,3,6-tetrahydropyridine, bis(hydrogen oxalate)

(Found: C, 49.57; H, 3.48;N, 7.23. C$_{24}$H$_{21}$N$_3$ClF$_3$O$_8$ 0.5H$_2$O requires C, 49.62; H, 3.81;N, 7.23%). $\delta_H$ (DMSO-d$_6$) 2.81 (2H, m, tetrahydropyridinyl CH$_2$), 3.07 (2H, m, tetrahydropyridinyl CH$_2$), 3.55 (2H, m, tetrahydropyridinyl CH$_2$), 4.04 (2H, s, NCH$_2$Ar), 6.79 (1H, m, C=CHCH$_2$), 7.46–7.55 (5H, m, ArH), 7.71 (1H, m, ArH), 7.89 (1H, s, ArH); m/z 392 (M+1)$^+$.

EXAMPLE 40

1-(4-Chlorobenzyl)-4-(5-methoxybenzimidazol-2-yl)-1,2,3,6-tetrahydropyridine

Mp. 203°–205° C. (MeOH); (Found: C, 53.35; H, 4.22;N, 7.65. C$_{20}$H$_{20}$ClN$_3$O, C$_4$H$_4$O$_8$, 0.25H$_2$O requires C, 53.34; H, 4.58;N, 7.80%); $\delta_H$ (DMSO-d$_6$) 2.94 (2H, m, tetrahydropyridyl CH$_2$), 3.28 (2H, m, tetrahydropyridyl CH$_2$), 3.75 (2H, m, tetrahydropyridyl CH$_2$), 3.90 (3H, s, OCH$_3$), 4.27 (2H, m, NCH$_2$Ar), 6.75 (1H, m, CH=CR), 6.93 (1H, dd, J 8.7, 1.2Hz, ArH), 7.13 (1H, d, J 1.2Hz, ArH), 7.54 (1H, d, J 8.7Hz, ArH), and 7.64 (4H, s, ArH); m/z 354 (M+1)$^+$.

We claim:

1. A method for the prevention and/or treatment of schizophrenia which method comprises administering to a patient in need of such treatment an effective amount of a compound of formula I, or a pharmaceutically acceptable salt thereof:

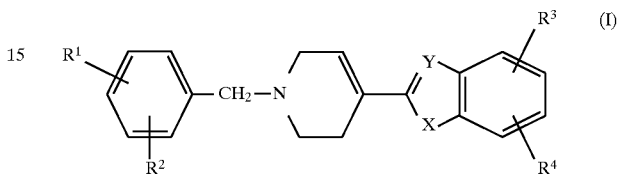

wherein

X represents sulphur;

Y represents nitrogen; and

R$^1$, R$^2$, R$^3$ and R$^4$ independently represent hydrogen, halogen, cyano, nitro, trifluoromethyl, C$_{1-6}$ alkyl or C$_{1-6}$ alkoxy.

2. The method as claimed in claim 1 wherein R$^1$ represents hydrogen, fluoro, chloro, bromo, cyano, nitro, methyl or methoxy.

3. The method as claimed in claim 1 wherein R$^2$ represents hydrogen or chloro.

4. The method as claimed in claim 1 wherein R$^3$ represents hydrogen, chloro, trifluoromethyl, methyl or methoxy.

5. The method as claimed in claim 1 wherein R$^4$ represents hydrogen or methyl.

6. The method as claimed in claim 5 wherein R$^4$ represents hydrogen.

7. A method for the prevention and/or treatment of schizophrenia which method comprises administering to a patient in need of such treatment an effective amount of a compound selected from the following:

4-(benzothiazol-2-yl)-1-benzyl-1,2,3,6-tetrahydropyridine;
4-(benzothiazol-2-yl)-1-(4-chlorobenzyl)-1,2,3,6-tetrahydropyridine;
4-(benzothiazol-2-yl)-1-(3-chlorobenzyl)-1,2,3,6-tetrahydropyridine;
4-(benzothiazol-2-yl)-1-(2-chlorobenzyl)-1,2,3,6-tetrahydropyridine;
4-(benzothiazol-2-yl)-1-(4-cyanobenzyl)-1,2,3,6-tetrahydropyridine;
1-benzyl-4-(5-chlorobenzothiazol-2-yl)-1,2,3,6-tetrahydropyridine;
4-(5-chlorobenzothiazol-2-yl)-1-(4-chlorobenzyl)-1,2,3,6-tetrahydropyridine;
4-(5-chlorobenzothiazol-2-yl)-1-(3-chlorobenzyl)-1,2,3,6-tetrahydropyridine;
4-(5-chlorobenzothiazol-2-yl)-1-(2-chlorobenzyl)-1,2,3,6-tetrahydropyridine;
1-benzyl-4-(5-trifluoromethylbenzothiazol-2-yl)-1,2,3,6-tetrahydropyridine.

8. The method of claim 7, wherein the compound is 4-(benzothiazol-2-yl)-1-(4-chlorobenzyl)-1,2,3,6-tetrahydropyridine or a pharmaceutically acceptable salt thereof.

* * * * *